United States Patent
Charles (10) Patent No.: US 10,507,134 B2
(45) Date of Patent: Dec. 17, 2019

(54) SYSTEMS AND METHODS FOR PULSED POSTERIOR VITREOUS DETACHMENT CREATION

(71) Applicant: Novartis AG, Basel (CH)

(72) Inventor: Steven T. Charles, Memphis, TN (US)

(73) Assignee: Novartis AG, Basel (CH)

( * ) Notice: Subject to any disclaimer, the term of this patent is extended or adjusted under 35 U.S.C. 154(b) by 408 days.

(21) Appl. No.: 15/162,803

(22) Filed: May 24, 2016

(65) Prior Publication Data

US 2016/0346122 A1    Dec. 1, 2016

Related U.S. Application Data

(60) Provisional application No. 62/166,807, filed on May 27, 2015.

(51) Int. Cl.
  *A61F 9/007* (2006.01)
  *A61B 17/3203* (2006.01)

(52) U.S. Cl.
  CPC ...... *A61F 9/00736* (2013.01); *A61B 17/3203* (2013.01); *A61F 9/00745* (2013.01)

(58) Field of Classification Search
  CPC .............................. A61F 9/007–9/0136; A61F 2009/00842–2009/00897; A61B 17/3203–17/32037; A61B 2017/32032–2017/32035
  See application file for complete search history.

(56) References Cited

U.S. PATENT DOCUMENTS

| | | | |
|---|---|---|---|
| 4,180,074 A * | 12/1979 | Murry | A61B 17/22012 604/118 |
| 5,066,276 A * | 11/1991 | Wang | A61F 9/00736 604/121 |
| 6,024,719 A * | 2/2000 | Morris | A61M 25/00 604/28 |
| 6,216,573 B1 * | 4/2001 | Moutafis | A61B 17/3203 417/413.1 |
| 6,413,245 B1 * | 7/2002 | Yaacobi | A61F 9/0017 604/264 |
| 7,141,048 B1 | 11/2006 | Charles | |
| 9,730,834 B2 | 8/2017 | Charles | |
| 2012/0191064 A1 * | 7/2012 | Conston | A61F 9/00727 604/506 |
| 2015/0164687 A1 | 6/2015 | Kashani et al. | |

* cited by examiner

*Primary Examiner* — Jonathan A Hollm (57) ABSTRACT

This disclosure relates to a tissue separation system to separate the posterior vitreous cortex from the inner limiting membrane in the eye, and to the separation of other body tissues. A system includes a flexible elongate member having a proximal end and a distal end. The flexible elongate member is coupled to a fluid reservoir and has a lumen configured to deliver fluid from the reservoir for use in a surgical procedure and further includes a pump system coupled to the proximal end of the flexible elongate member and to the fluid reservoir, configured to pressurize the fluid to a pressure suitable for separating tissues. The system also includes a control system arranged to control the pump system to provide a series of pulses of fluid through the flexible elongate member and out from the distal end thereof to suitably separate the tissues during the surgical procedure.

11 Claims, 10 Drawing Sheets

SYSTEMS AND METHODS FOR PULSED POSTERIOR VITREOUS DETACHMENT CREATION

TECHNICAL FIELD

The present disclosure relates to apparatuses and methods for ophthalmic medical procedures, and more particularly, to apparatuses and methods including separation of the vitreous humor from the retina.

BACKGROUND

Many microsurgical procedures require precision cutting, removal, and/or separation of various body tissues. For example, certain ophthalmic surgical procedures require the cutting and/or removal of the vitreous humor, a transparent jelly-like material that fills the posterior segment of the eye. The vitreous humor, or vitreous, is composed of numerous microscopic fibrils that are often attached to the retina by the posterior vitreous cortex. Therefore, cutting and removal of the vitreous must be done with great care to avoid traction on the retina, the separation of the retina from the retinal pigment epithelium, a retinal tear, or, in the worst case, retinal detachment. Delicate operations such as mobile tissue management (e.g., cutting and removal of vitreous near a detached portion of the retina or a retinal tear), vitreous base dissection, and cutting and removal of membranes are particularly difficult.

With age, the vitreous may naturally contract and separate from the retina and, generally, this occurs without negatively affecting the vision or health of a person's eyes. However, in some instances the vitreous may detach from some portions of the retina without detaching from others. This may cause a contracting vitreous to pull on the retina, distorting vision and potentially causing a tear also called a retina break, potentially leading to retinal detachment. Other conditions such as vitreomacular traction, resulting from the vitreomacular adhesion and vitreomacular schisis are a result of incomplete separation of the vitreous humor from the posterior retina. The condition may be treated by attempting to mechanically detach the adhered portion of the vitreous from the retina.

Detaching adherent vitreous can be accomplished using standard vitrectomy probes. These typically include a hollow needle with a port on the end to pull in fibrils forming the vitreous humor. An inner member, placed within the hollow needle, moves back and forth to open and close the port. This operates to cut any fibrils that enter the port while it is open. The motion used to position vitreous within the hollow needle may be a back and force motion tangential to the surface of the retina that places significant sheer stress on the delicate retina through the posterior vitreous cortex. Another approach relies on enzymes to chemically separate the vitreous from the retina. While this approach may be effective, it may also generate unwanted side effects. Accordingly, the current approaches are not satisfactory in all respects.

SUMMARY

This disclosure relates generally to, and encompasses, systems and methods for separating one layer of body tissue from another, such as separating a posterior vitreous cortex from the inner limiting membrane (ILM), and more specifically to ophthalmic surgical systems and methods of using the systems to generate posterior vitreous detachment sites to alleviate vitreomacular adhesion (VMA) and treat vitreomacular traction. Separation of the vitreous from the retina is also required to treat some types of retinal detachment typically in younger, near-sighted patients and trauma patients.

According to one example, this disclosure relates to a tissue separation system that may include a flexible elongate member having a proximal end and a distal end. The flexible elongate member may be coupled to a fluid reservoir and may have a lumen configured to deliver fluid from the reservoir for use in a surgical procedure. The tissue separation system may further include a pump system coupled to the proximal end of the flexible elongate member and to the fluid reservoir, and may be configured to pressurize the fluid to a pressure suitable for separating a first body tissue from a second body tissue. The tissue separation system also may include a control system in communication with the pump system. The control system may be arranged to control the pump system to provide a series of pulses of fluid through the flexible elongate member and out from the distal end of the flexible elongate member to suitably separate the first body tissue from the second body tissue during the surgical procedure.

According to another example, an ophthalmic surgical system for posterior vitreous detachment is described. The surgical system may include a handpiece that may have a flexible elongate member with a proximal end and a nozzle at a distal end. The proximal end may be configured to couple to a fluid reservoir for use in a surgical procedure. And the nozzle may be arranged to emit fluid in a manner that separates a first body tissue from a second body tissue. The surgical system may include a pump system coupled to the proximal end of the flexible elongate member and to the fluid reservoir and may include a control system in communication with the pump system. The control system may cause the pump system to provide a series of pulses of fluid through the flexible elongate member, the series of pulses being expelled from the nozzle of the flexible elongate member to separate the first body tissue from the second body tissue.

According to yet another example, a method of performing a surgery that may include receiving a command from a user of a surgical system to initiate a detachment process, forcing a first pulse of fluid from a fluid reservoir of the surgical system through a lumen of a flexible elongate member in a handpiece to a surgical site to separate a first body tissue from a second body tissue, and forcing a second pulse of fluid from the reservoir of the surgical system through the lumen to the surgical site to further separate a first body tissue from a second body tissue, is disclosed.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates to devices, systems, and methods for separating tissues, particularly ocular tissues, and more particularly adhered layers of tissues. The various figures show embodiments of exemplary ophthalmic surgical systems and devices and methods of using the devices to separate delicate tissues within a patient's eye. Embodiments described herein incorporate pulsed fluid aspects of a system that may operate to cause separation of the vitreous from the retina during a procedure to treat vitreomacular traction, vitreomacular schisis or retinal detachment, which if left untreated may result in vision distortion or vision loss. One of ordinary skill in the art, however, would understand that similar embodiments could be used to separate delicate tissues in other locations in the body without departing from the general intent or teachings of the present disclosure.

Figure 1A:
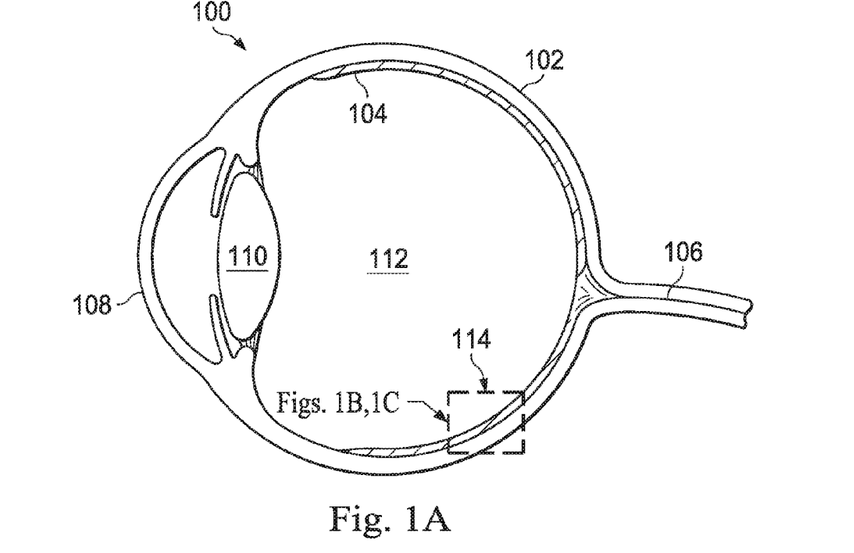
FIG. 1A is a cross-sectional illustration of an eye of a patient.

FIG. 1A is a cross-sectional illustration of an eye 100. A number of features of the eye 100 are illustrated herein. The eye 100 includes a sclera 102 that is coupled to a retinal membrane or retina 104 by a choroid. The choroid includes the retinal pigment epithelium to attach the retina 104 to the inside wall of the sclera 102 at the back of the eye 100 and to provide oxygen and nourishment to the outer layers of the retina 104. A cornea 108 permits light to enter the eye 100, the light being focused by a lens 110 through a vitreous chamber onto the retina 104, which contains photo-activated cells that transmit signals over the optic nerve 106 to the brain. The vitreous chamber is filled with vitreous humor 112 or, simply, vitreous 112 that includes a clear gelatinous hyaluronan material including collagen fibers distributed therein. The vitreous 112 is in contact with the innermost layer of the retina 104.

Figure 1B:
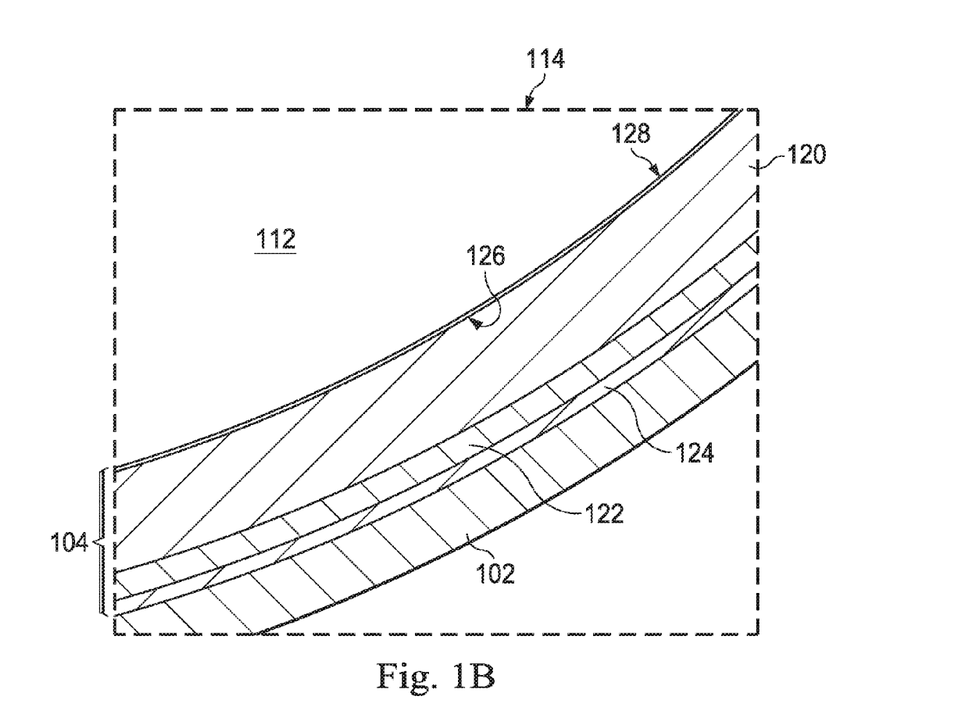
FIG. 1B is a cross-sectional illustration of a normal portion of the retina of the eye.

FIG. 1B illustrates in greater detail an area of interest 114 of the eye 100. FIG. 1B shows an eye 100 in a normal condition in close-up to provide greater, schematic detail of the tissue layers of the retina 104. The laminated or layered tissues present in the eye 100 are not drawn to scale. As shown in FIGS. 1A and 1B, the retina 104 includes several layers, including a main retinal layer 120, a sub-retinal space 122, and an opaque layer 124. The retinal layer 120 includes an inner limiting membrane (ILM) 126 that is in contact with the posterior vitreous cortex 128 of the vitreous humor 112 that fills the vitreous chamber. The retinal layer 120 further includes a nerve fiber sub-layer, a ganglion cell sub-layer, an inner plexiform sub-layer, an inner nuclear sub-layer, an outer plexiform sub-layer, and an outer nuclear sub-layer. The retinal layer 120 also includes an external limiting membrane and a photoreceptor sub-layer. The opaque layer 124 includes the retinal pigment epithelium (RPE) and the choroid.

Figure 1C:
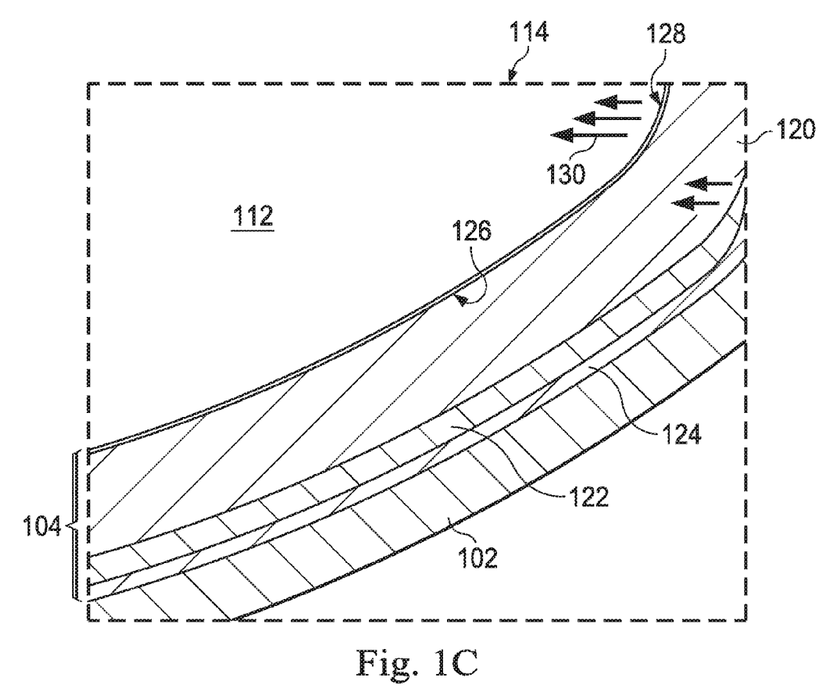
FIG. 1C is a cross-sectional illustration of a symptomatic portion of the retina of the eye shown in FIG. 1.

As shown in FIG. 1B, the posterior vitreous cortex 128 is in continuous contact with the ILM 126. However, in human eyes it is common for the vitreous 112 to decouple or detach from the retina as age increases. However, in some instances the detachment may be not complete, such that a portion of the vitreous 112 may adhere to the retina 104 even while the vitreous 112 contracts, as is shown in the area of interest 114 of the eye 100 of FIG. 1C. When this occurs, the contraction of the vitreous 112 exerts a force 130 on the retina 104. This force may cause the retina 104 to bend unnaturally, as shown in FIG. 1C, or to tear in some cases. Accordingly, there is a desire to be able to detach the vitreous 112 from the retina 104 to prevent damage to the retina 104 and to prevent associated visual distortion and/or loss of sight.

Figure 2:
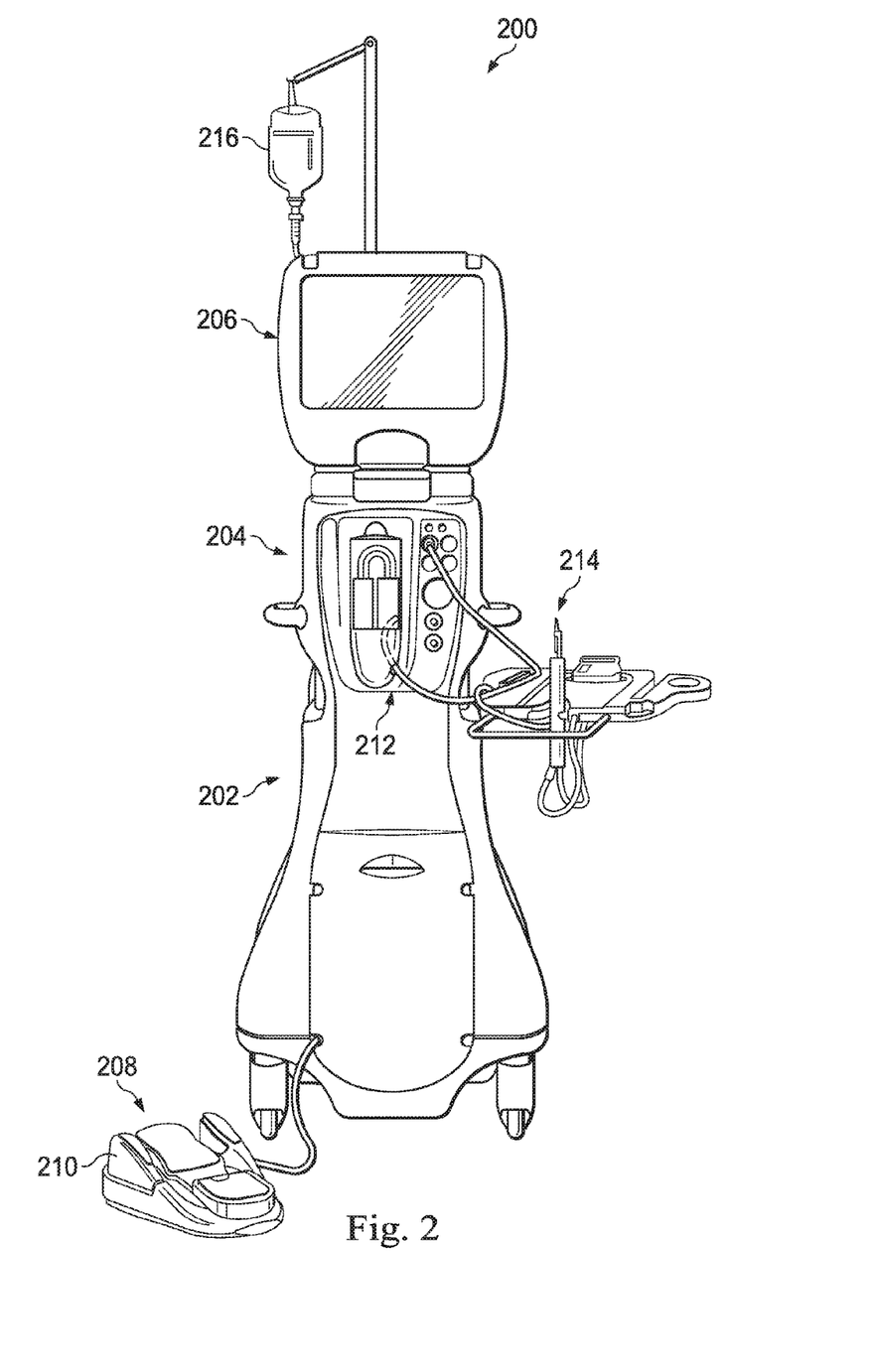
FIG. 2 is an illustration of an exemplary surgical system according to aspects implementing the teachings and principles described herein.

FIG. 2 illustrates an exemplary ophthalmic surgical system, shown as a console 200. The console 200 includes a base housing 202 with a controller or computing subsystem 204 and an associated display screen 206 adapted to show data relating to system operation and performance during a posterior vitreous detachment (PVD) procedure. The console 200 also includes a number of subsystems that may be used together to perform surgical procedure to separate one body tissue from another, such as separating the vitreous 112 from the retina 104 of FIG. 1. For example, the subsystems may include one or more of a foot pedal subsystem 208 including a foot pedal 210 having a number of foot-actuated controls and a fluidics subsystem 212 including a hand-held surgical separation device shown as hand piece 214. The hand piece 214 may include components that allow a clinician to direct a series of pulses of fluid to a surgical site near the posterior of the eye to separate adhered tissues.

In some embodiments, the console 200 further includes an ultrasonic generator subsystem within the housing 202 that is operable to cause a phacoemulsification tip of a hand piece to oscillate ultrasonically. Some embodiments of the console 200 further include a pneumatic vitrectomy cutter subsystem with a vitrectomy hand piece. The pneumatic vitrectomy cutter subsystem may be coupled to or be part of the fluidics subsystem 212 to provide pressurized air to power the vitrectomy hand piece.

The fluidics subsystem 212 may include one or more reservoirs of fluid that may be used in a surgical procedure. As illustrated in FIG. 2, the console 200 includes a reservoir 216. The reservoir 216 may contain a fluid to be injected into the eye or another part of the body in a series of pulses. In some embodiments, the fluid in the reservoir 216 is air and the reservoir 216 is a tank of compressed gas. In other embodiments, the reservoir 216 may contain a balanced salt solution (BSS), a perfluorocarbon liquid such as perfluoro-n-octane (PFO), hydroxypropyl methylcellulose (HPMC), hyaluronic acid, chondroitin sulfate, or another viscoelastic. The fluid in the reservoir 216 may be a non-Newtonian, pseudoplastic, viscoelastic fluid, in some embodiments. Additionally, the reservoir 216 may contain air. Some embodiments of the fluidics subsystem 212 may include other reservoirs in addition to the reservoir 216. For example, the fluidics subsystem 212 may include a pump or a compressor that is controlled by the computing subsystem 204 to generate a series of pulses of one or more fluids contained in corresponding one or more reservoirs. The fluidics subsystem 212 provides for the control of pressure and/or volume of fluids expelled from the fluidics subsystem 212.

These subsystems of console 200 may overlap, in some embodiments, and cooperate to perform various aspects of a procedure and may be operable separately and/or independently from each other during one or more procedures. That is, some procedures may utilize one or more subsystems while excluding others.

Figures 3, 4:
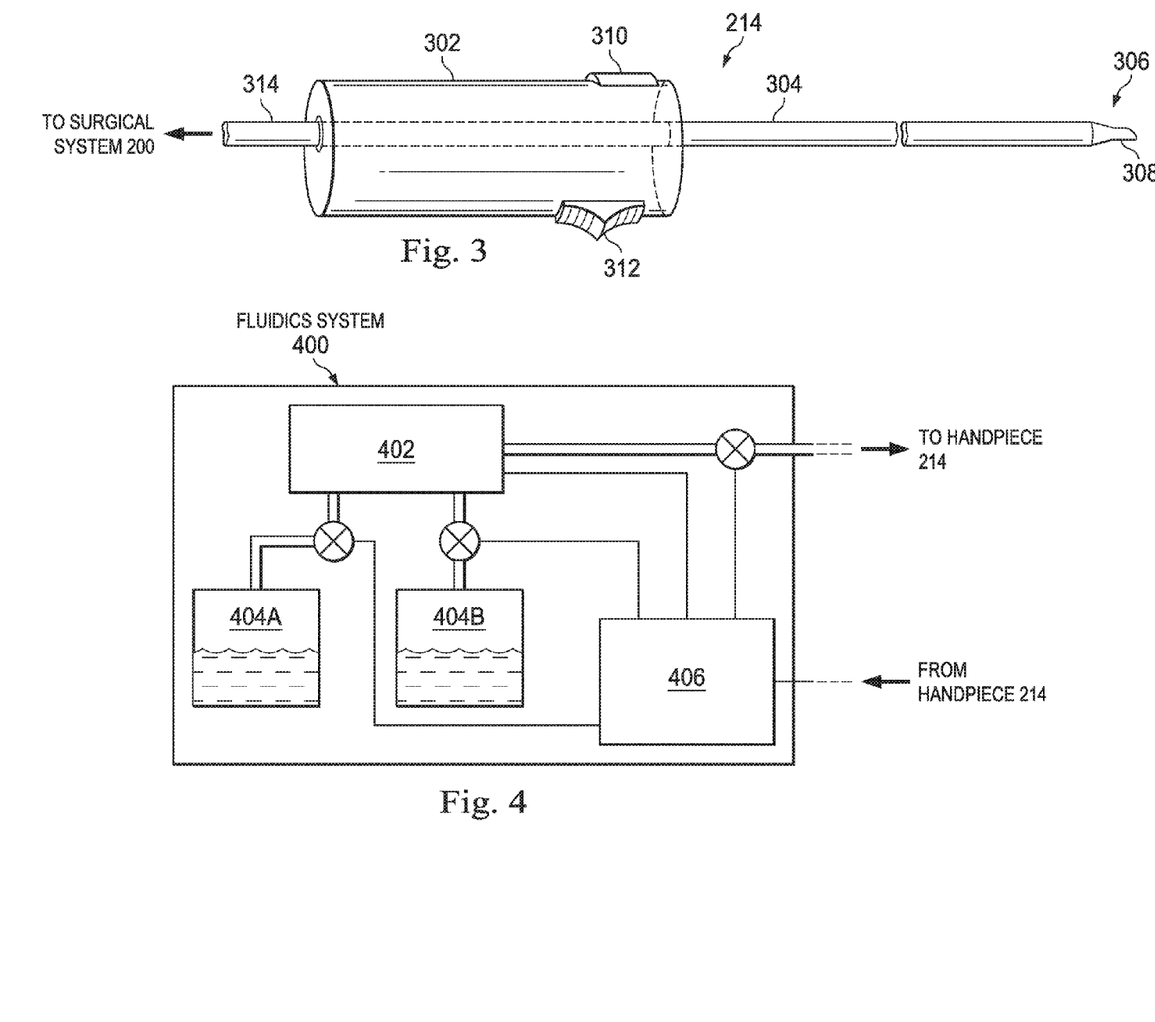
FIG. 3 is a diagram of a surgical probe with a flexible elongate member for insertion into the eye of a patient according to one example of principles described herein.
FIG. 4 is a functional diagram illustrating some of the components of the surgical system according to aspects of the present disclosure implementing the teachings and principles described herein.

FIG. 3 is a stylized diagram showing a portion of the illustrative tissue separation hand piece 214. According to the present example, the hand piece 214 includes a body 302 and a flexible elongate member 304 having a lumen therethrough through which a fluid may pass toward a distal end 306. The body 302 forms a handle portion that may be grasped and manipulated by a surgeon when performing a surgical procedure, such as a posterior vitreous detachment (PVD) procedure. In some embodiments, the exterior portion of the body 302 is ergonomically designed for comfortable grasping by the surgeon. The body 302 may be made from a variety of materials commonly used to form such tools. For example, the body 302 may be made of, for example, a lightweight aluminum, a polymer such as polyether ether ketone (PEEK), or another material. Depending on the embodiment, it may be sterilized and used in more than one surgical procedure, or it may be a single-use device.

In the illustrated embodiment, the distal end 306 of the flexible elongate member 304 includes a tapered section with a nozzle portion 308 that may be used to direct the fluid as it is ejected under pressure from the flexible elongate member 304. The flexible elongate member 304 may be a flexible cannula sized for insertion into the eye of a patient through a surgical opening therein. The body 302 is coupled to the flexible elongate member 304 such that the distal end 306 thereof may be manipulated by a clinician by manipulating the body 302. In some embodiments, the flexible elongate member 304 includes a pre-formed bend at the distal end.

The body 302 may include one or more buttons, knobs, or other physical interface elements to permit the clinician to adjust certain aspects of the performance of the surgical system 200. As illustrated, the body 302 includes a toggle switch or button 310 that may be used to start and stop a series of pulses of fluid being emitted from the nozzle portion 308. The body 302 further includes a slider 312 that permits the clinician to adjust at least one characteristic of individual pulses or of the series of pulses between two extreme positions. For example, the slider 312 may control a volume of each of the pulses of fluid between 100 microliters and 10 microliters. Other volume amounts or ranges may be used in other embodiments, and higher and lower volumes are contemplated. In other embodiments, the slider 312 controls the pressure at which the fluid is ejected from the nozzle portion 308. For example, a maximum pressure may be 30 pounds per square inch (PSI) in some embodiments. In general, the pressure of the fluid may be inversely proportional to the viscoelasticity of the fluid injected by the hand piece 214 into the eye of the patient. Accordingly, a pressure of 30 PSI may be more appropriate when the fluid injected is viscoelastic. In some embodiments, the slider 312 may control the rate of the series of pulses, such that the clinician may be able to increase or decrease the pulsation rate. Other embodiments of the hand piece 214 may include sliders or other physical interface elements for each of these functions and more. Additionally, in some embodiments, the console 200 may provide physical user interface elements or virtual user interface elements whereby the clinician or an assistant may control characteristics of the individual pulses or the series of pulses.

In other embodiments, the control of each pulse or series of pulses in terms of pulse volume, pulse pressure, pulse frequency, pulse duration, etc. may be controlled individually or collectively by the foot pedal subsystem 208. Specific characteristics of an individual pulse or series of pulses may be controlled by one or more footswitches like the footswitch 210. Additionally, a graphical user interface (GUI) may be provided by the console 200, and a clinician may provide user controls to control pulse characteristics and may start and stop generation of pulses using the foot pedal subsystem 208 in connection with the GUI. For example, characteristics of the pulse or pulses may be set or adjusted by interaction with the GUI and the starting and stopping of pulses may be controlled by the footswitch 210.

Within the body 302, the lumen of the flexible elongate member 304 connects to a conduit 314 that couples the hand piece 214 to the fluidics subsystem 212 of the surgical system 200 of FIG. 2. The conduit 314 may include a flexible elongate member that couples the flexible elongate member 304 to the reservoir 216 or to another reservoir or to a pump system coupled to one or more reservoirs. Additionally, the conduit 314 includes electrical connections between the button 310 and the slider 312 on the body 302 to the computing system 204. In some embodiments, commands to adjust the pressure, volume, and rate of the series of pulses may be received by the clinician's manipulation of the foot pedal subsystem 208 rather than, or in addition to, commands issued via the components of the hand piece 214.

Referring now to FIG. 4 shown therein is a diagram of a fluidics subsystem 400 that may be included in embodiments of the console 200 as the fluidics subsystem 212. As illustrated, the fluidics subsystem 400 includes a pump system 402 that is coupled to a reservoir 404A and to a reservoir 404B. The pump system 402 removes fluid from one of the reservoirs 404A and 404B for injection into the eye of the patient through the flexible elongate member 304 as described herein. The fluidics subsystem 400 further includes a control system 406 that is electronically and communicatively coupled to the pump system 402 and to a plurality of valves incorporated into the fluidics subsystem 400. In some embodiments, the control system 406 may be provided by the computing system 204 of FIG. 2 and may provide electrical signals to open and close the plurality of valves and/or to control a pump within the pump system 402. In some embodiments, the pump system 402 includes a diaphragm pump or peristaltic pump; other embodiments may include other types of pumps as may be apparent to one of skill in the art. For example, the control system 406 may receive a command from the hand piece 214 to increase the pressure provided by the pump system 402. The control system 406 may interpret the command from the hand piece 214 and provide the appropriate signals to the pump system 402 to increase the pulse pressure.

In some embodiments of the fluidics subsystem 400, one or more components may be provided in the hand piece 214. For example, the pump system 402 and the control system 406 may be provided within the body 302. In such embodiments, the body 302 may include one or more internal reservoirs. The internal reservoirs may be filled and replenished from the reservoirs 404A and/or 404B. The pump system 402 may pull fluid from the reservoirs 404A and 404B and force the fluid out of the body 302, through the flexible elongate member 304, under a desired pressure at a desired rate in pulses containing a desired volume per pulse.

In some embodiments of the fluidics subsystem 400, one of the reservoirs 404A and 404B includes a dye that may be combined with another fluid to make that other fluid visible when injected into the patient to separate tissues. For example, the reservoir 404A may include a balanced salt solution while the reservoir 404B includes a visible dye. The fluidics subsystem 400 may be configured to mix fluids from both the reservoir 404A and the reservoir 404B prior to injection into the patient in a series of pulses. In some embodiments, the fluid injected into the patient may include an active chemical or biological component, such as an enzyme, that reacts with a feature at the surgical site. For example, in some embodiments the fluid injected in a series of pulses includes ocriplasmin, a protease that can dissolve the proteins that secure the vitreous 112 to the retina 104. In such embodiments, the series of pulses creates a posterior vitreous detachment through the application of pressure and through an enzymatic reaction. Other chemical or biological components may be used in other embodiments.

Figure 5A:
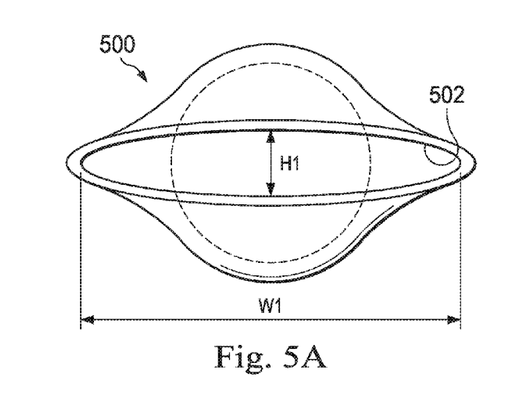
FIGS. 5A, 5B, and 5C are three views of a distal end of the flexible elongate member of the surgical probe illustrated in FIG. 3 according to one example incorporating the principles described herein.
Figure 5B:
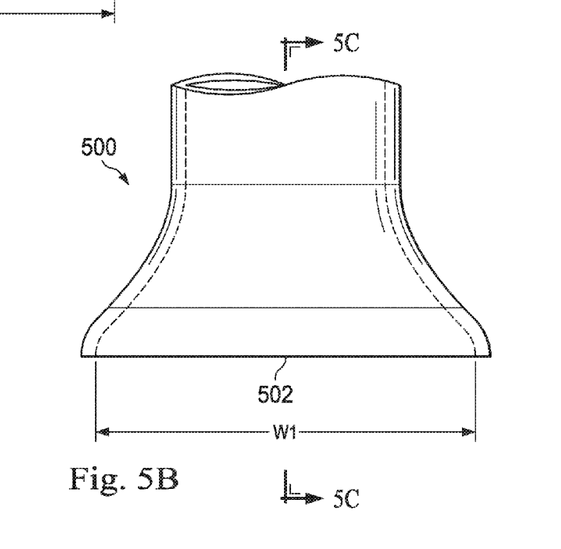
Figure 5C:
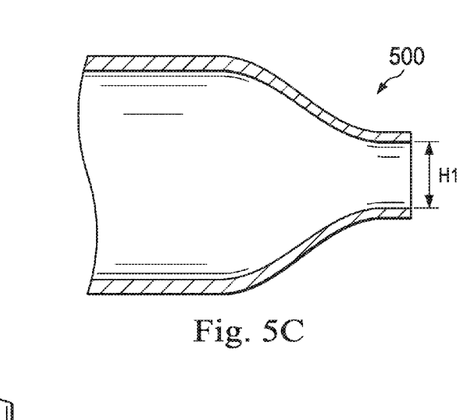

Referring now to FIGS. 5A, 5B, and 5C, shown therein are three views of a nozzle portion 500 of a flexible elongate member such as the flexible elongate member 304 of FIG. 3. In some embodiments of the surgical system described herein, a nozzle is included at the distal end of the flexible elongate member 304 in order to more effectively direct the fluid as it is injected into the eye of a patient to separate one tissue from another. FIG. 5A is an "end on" view that depicts an opening 502 in the nozzle portion 500, which has an enlarged, spatula-like shape. The opening 502 is depicted as being generally oval in shape and having a width W1 and a height H1. In some embodiments, the opening 502 and other such slit-like openings described herein, may have an elliptical opening, a rectangular opening, or an opening having another shape. The shape may be symmetric or asymmetric relative to the width and/or height of the opening. Additionally, some embodiments may include a plurality of openings. While, as illustrated, the width W1 is greater than the diameter of the flexible elongate member (including the thickness of the flexible elongate member and the diameter of the lumen therethrough), the height H1 is less than the diameter of the flexible elongate member. This may be seen in the top view of the nozzle portion 500 as shown in FIG. 5B and in the cross-sectional side view of FIG. 5C, respectively. The cross-sectional side view of FIG. 5C is viewed along the line 5C-5C of FIG. 5B.

Figure 5D:
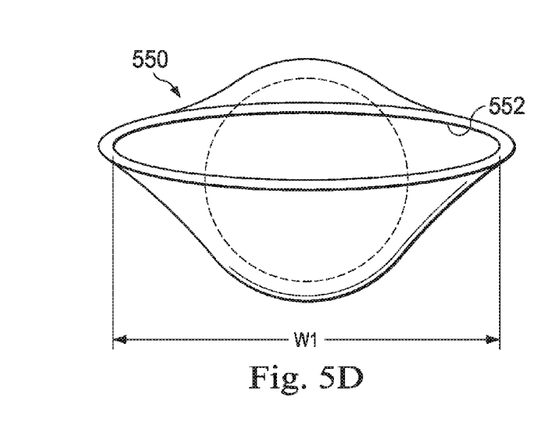
FIGS. 5D, 5E, and 5F are three views of a distal end of the flexible elongate member of the surgical probe illustrated in FIG. 3 according to another example incorporating the principles described herein.
Figure 5E:
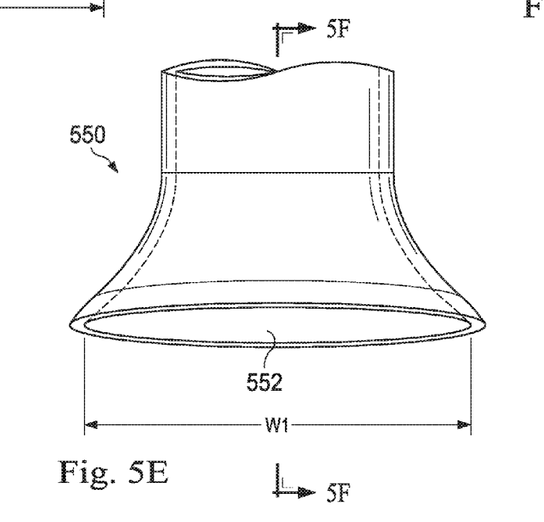
Figure 5F:
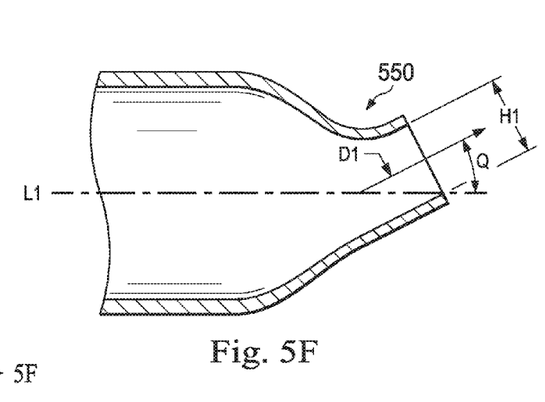

Referring now to FIGS. 5D, 5E, and 5F, shown therein are three views of a nozzle portion 550 of a flexible elongate member such as the flexible elongate member 304 of FIG. 3. The nozzle portion 550 is similar to the nozzle portion 550 in many respected. While the nozzle portion 500 is configured to direct fluid along the luminal axis of the flexible elongate member, the nozzle portion 550 directs fluid away from the luminal axis at an angle θ. By directing the nozzle portion 550 at the angle θ in a direction D1, rather than along the luminal axis L1, the fluid may be directed slightly away from the ILM 126 and the rest of the retina 104. In this way, damage to the retina 104 during posterior vitreous detachment may be further minimized. FIG. 5D is an "end on" view that depicts an opening 552 in the nozzle portion 550, which has an enlarged, spatula-like shape. The opening 552 is depicted as being generally oval in shape and having a width W1 and a height H1, better observed in the cross-sectional view of FIG. 5E. In other embodiments, the nozzle portion 550 may curve away from the luminal axis L1. The curve or angle at which embodiments of the nozzle portion 550 directs the fluid away from the luminal axis may range from about 10° to about 60° or more. The cross-sectional side view of FIG. 5C is viewed along the line 5C-5C of FIG. 5B.

Figure 6A:
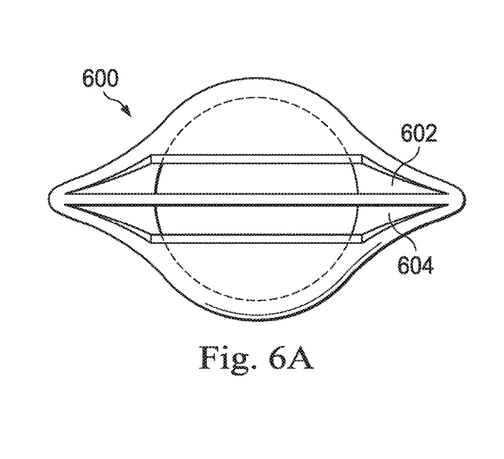
FIGS. 6A, 6B, and 6C are three views of a distal end of the flexible elongate member of the surgical probe illustrated in FIG. 3 according to another example incorporating the principles described herein.
Figure 6B:
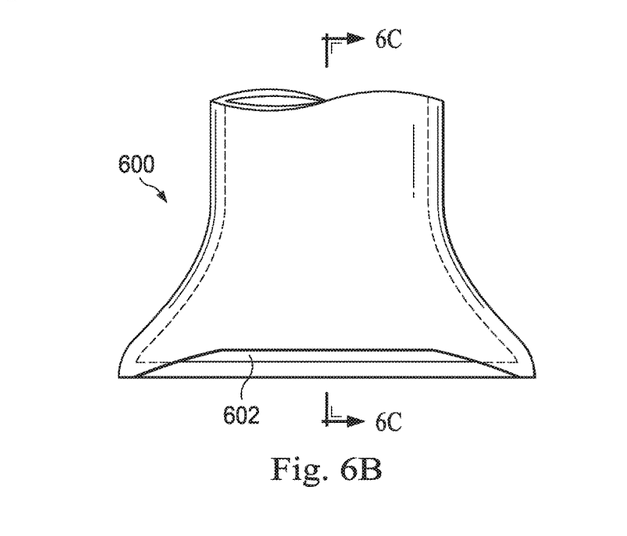
Figure 6C:
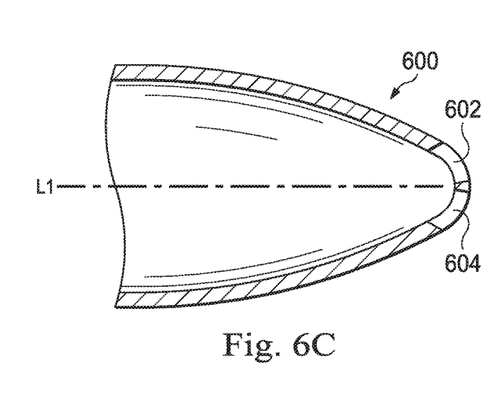

Shown in FIGS. 6A, 6B, and 6C is a nozzle portion 600 that may be included at the distal end of the flexible elongate member to be inserted into the eye of a patient to facilitate in carefully separating the vitreous 112 from the retina 104 with minimal tearing or stressing of the retina 104. The nozzle portion 600 is similar in many respects to the nozzle portion 500; however, the nozzle portion 600 includes two openings rather than one. The nozzle portion 600 includes a side port 602 on an upper side and a side port 604 on the lower side of a distal tip of the nozzle portion 600. In some embodiments, additional side ports may be present. As illustrated, the side ports 602 and 604 direct fluid away from the distal end of the flexible elongate member in directions that are off the central, lengthwise axis L1 of the flexible elongate member 304. Depending on the orientation of the flexible elongate member and its positioning proximate the retina 104 and the vitreous 112, one of the side ports directs fluid toward the retina 104 while the other side port directs fluid toward the vitreous 112. In some embodiments, one of the side ports may direct fluid along the axis L1, while the other side port directs fluid away from axis L1 at an angle as shown in FIGS. 5C, 5D, and 5E. FIG. 6A provides an end on view of the nozzle portion 600, while FIG. 6B provides a top view thereof. FIG. 6C is a cross-sectional view of the nozzle portion 600 as seen according to the line 6C-6C of FIG. 6B.

Figure 7A:
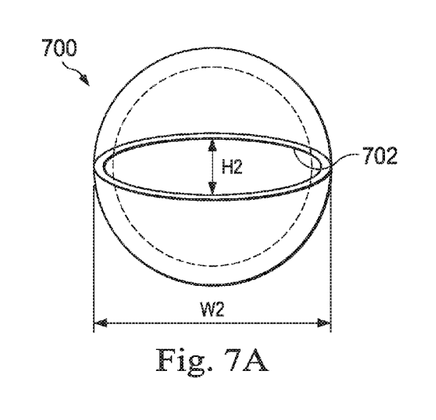
FIGS. 7A, 7B, and 7C are three views of a distal end of the flexible elongate member of the surgical probe illustrated in FIG. 3 according to another example incorporating the principles described herein.
Figure 7B:
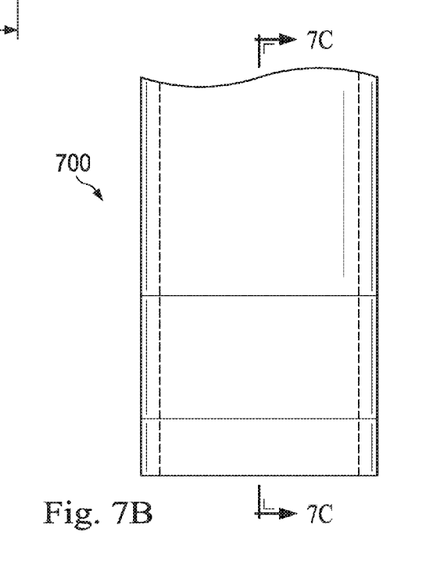
Figure 7C:
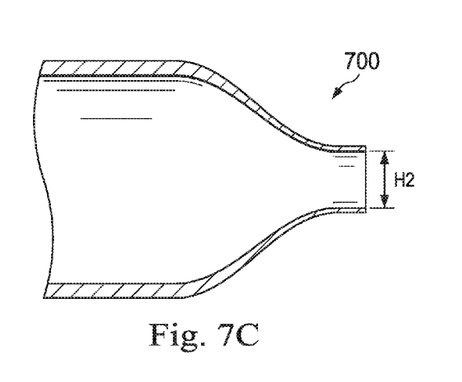

Referring now to FIGS. 7A, 7B, and 7C, shown therein is yet another embodiment of a distal end of the flexible elongate member. The nozzle portion 700 includes an opening 702 having a width W2 and a height H2. The nozzle portion 700 is similar to the nozzle portion 500 in many respects. However, the width W2 is not greater than the diameter of the flexible elongate member. A top view is included in FIG. 7B, while a cross-sectional view is presented in FIG. 7C according to the line 7C-7C of FIG. 7B.

The nozzle portions 500, 550, 600, and 700 present only a few embodiments of the nozzle 308 of FIG. 3, and aspects may be combined in various embodiments. In some embodiments, the opening or openings may have a different shape, such as a rectangular shape, and there may be more than two openings. In some embodiments, the nozzles may be made of a polymer or a metal alloy such as nitinol. Some embodiments of the nozzles 600 and 700 may be configured, like the nozzle 550, to direct fluid away from the luminal axis of the flexible elongate member 304, in order to prevent damage to the retina 104. In general, the nozzle portions 500, 550, 600 and 700 direct the fluid injected in a series of pulses that separate the posterior vitreous cortex 128 from the ILM 126 in order to prevent damage to the retina 104.

Figure 8:
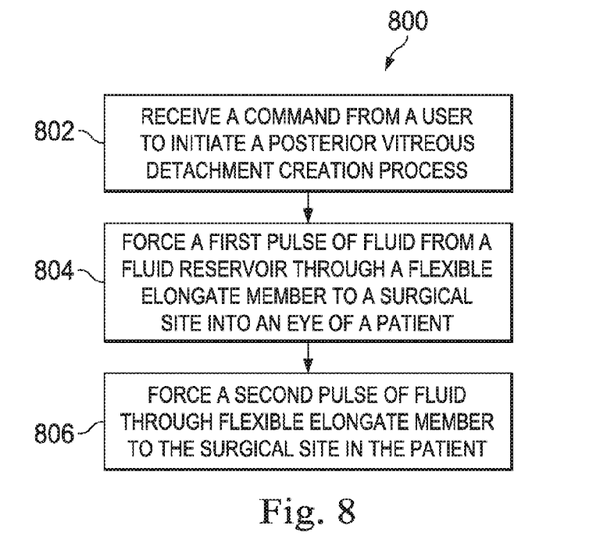
FIG. 8 is a flowchart showing an illustrative method for performing a surgery to separate tissues according to one example incorporating the principles described herein.

Referring now to FIG. 8, shown therein is a flowchart of a method 800 for performing a surgical procedure to separate tissues, such as a posterior vitreous cortex from an ILM. As shown in FIG. 8, the method 800 includes several elements or operations. Embodiments of the method 800 may include additional elements or operations before, after, in between, and/or as part of the enumerated elements. The elements of the method 800 may be performed by a surgical system, such as the surgical system 200 of FIG. 2 and as described herein.

In the performance of an exemplary method 800, a clinician may make a small opening in the posterior vitreous cortex with a surgical instrument, such as a curved tip, flexible cannula. The cannula may be further configured to direct a series of pulses of fluid injected in between the posterior vitreous cortex and the ILM. In other embodiments, a second surgical instrument is used to provide the series of pulses after the opening is made. Once the surgical instrument capable of directing pulses of fluid to the interface between the posterior vitreous cortex and the ILM is in place, the clinician may use a button on a hand piece, such as the hand piece 214, or a foot pedal, such as the foot pedal 210 to direct a surgical system to initiate a posterior vitreous detachment creation process.

At 802, a control system receives a command from the user to initiate the posterior vitreous detachment process. This command may be received by the control system from the user when the user manipulates a switch or other physical interface element. The control system may be the computing subsystem 204 of the console 200, illustrated in FIG. 2 or the control system 406 of FIG. 4. The computing subsystem 204 includes a plurality of subcomponents in order to receive, process, and issue commands to control a series of pulses to separate tissues. The control system includes one or more processing devices, such as central processors or microcontrollers. The processing devices may be present in multiple components of the console 200. For example, the console may include a first processing device and the hand piece 214 may include a second processing device.

The control system interprets the received command and directs, at 804, a pump system to force, expel, or inject a first pulse of fluid from a fluid reservoir through a flexible elongate member to a surgical site within the patient, such as at a posterior portion of the eye of the patient. For example, the control system 406 may include a microcontroller that directs the pump system 402 to generate a pulse of fluid. As directed, the pump system 402 may actuate a diaphragm pump, a peristaltic pump, or another type of pump, and cause fluid in the pump to be expelled through the flexible elongate member 304 of the hand piece 214, and into the eye of the patient. Depending on the pump system 402, the pulse of fluid may correspond to a single pump cycle. For example, when the pump system includes a diaphragm pump, a single pulse may be provided by a single pump cycle. In such embodiments, controlling aspects of the pulse may be provided by adjusting a pump volume, adjusting a pump frequency, adjusting a pump force, etc. The pump system 402 may include one or more valves to ensure that the first pulse of fluid is injected into the eye rather than drain from the eye. In some other embodiments, the pump system 402 provides a source of continuous pressure that is released in a series of pulses by actuating a valve to generate the series of pulses of fluid.

Figure 9:
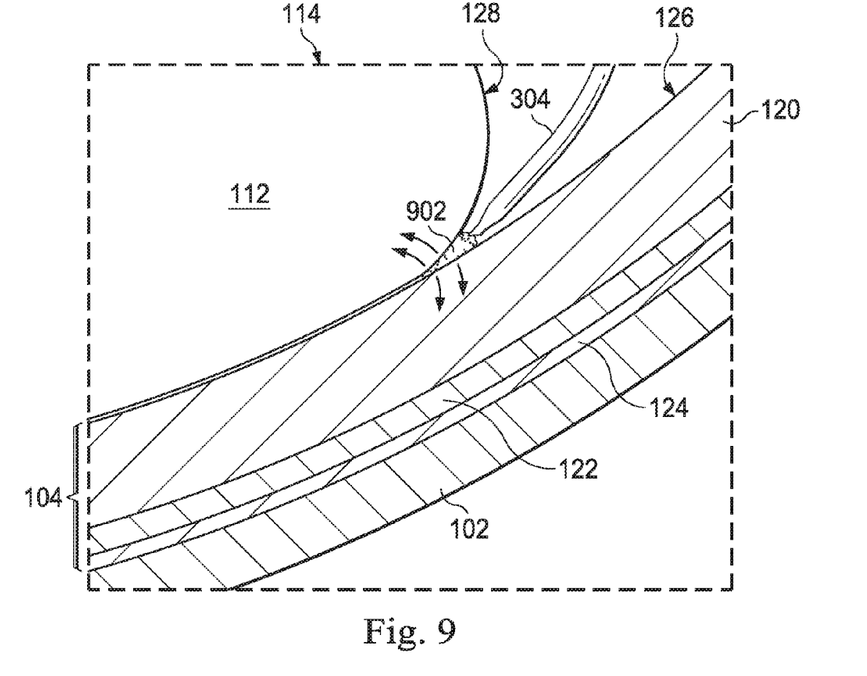
FIG. 9 is a diagram of an exemplary surgical procedure utilizing a surgical system according to one example of principles described herein.

FIG. 9 is a diagram of an exemplary surgical procedure utilizing a surgical system according to one example of the principles described herein to illustrate the application of a pulse of fluid as described herein. FIG. 9 is similar in many respects to FIGS. 1B and 1C, showing vitreous 112 being detached from the retina 104. As shown in FIG. 9, a flexible elongate member 304 is inserted between the posterior vitreous cortex 128 and the ILM 126. When a pump system is activated by control system to force a pulse of fluid 902 (or pulse 902) out of the nozzle portion 308, the pulse 902 produces a pressure against the vitreous 112 and the retina 104 to separate these two tissues. Because the fluid does not have hard or sharp edges, the pulse 902 may minimize potential damage to the retina 104. The fluid may also distribute the force along a greater area. Thus, the use of fluid may provide a safer approach to posterior vitreous detachment creation than current methods that rely on a vitreous cutter to perform a vitrectomy that can expose the retina to tangential forces. The pressure applied by the pulse 902 may be controlled by the selection of the fluid and/or by control of the pump system 402. For example, when the pulse 902 is a pulse of air the pump system 402 may be set to provide a higher pressure than when the pulse 902 is a non-Newtonian fluid.

When the fluid includes an enzyme such as ocriplasmin, or another such active component, both the enzyme and the application of pressure may be used to separate the two tissues. In such embodiments, the rate of pulsation and/or other aspects of the series of pulses may be adjusted to accommodate the chemically or biologically active component. For example, a pressure may be decreased in view of the concentration of the active component in the fluid. Additionally, in some embodiments the rate of pulsation may be decreased as active components are included in the fluid and/or the concentration of such active components is increased. Because the application of pressure is also relied upon to separate the tissues, the concentration and/or quantity of active component may be less than that required when only the active component is relied upon to separate the tissues. In instances in which the active component may produce unwanted side effects, the combination of the application of a series of pulses as described herein may decrease the production of such side effects.

Referring again to FIG. 8, after the first pulse of fluid is forced to the surgical site, at 806, a second pulse of fluid may be forced through the flexible elongate member to the surgical site within the patient. Between 804 and 806, the clinician may advance the flexible elongate member to better position the nozzle portion 308. For example, the injection of the first pulse of fluid into the eye of the patient may increase an area of detachment between the vitreous 112 and the retina 104 (i.e., may increase the posterior vitreous detachment). In order to increase the efficiency of any subsequent pulses, the clinician may advance the nozzle portion 308 closer to regions of maintained attachment. In some embodiments, the position of the nozzle portion 308 may be maintained for more than one pulse before the nozzle portion 308 is advanced.

In this manner, a series of pulses may be injected into the eye of the patient between the posterior vitreous cortex 128 and the ILM 126. The pressure of the series of pulses may cause the posterior vitreous cortex 128 and the ILM 126 to separate without applying shear stress to the retina 104. This may increase the safety and efficacy of posterior vitreous detachment creation as described herein.

Figure 10:
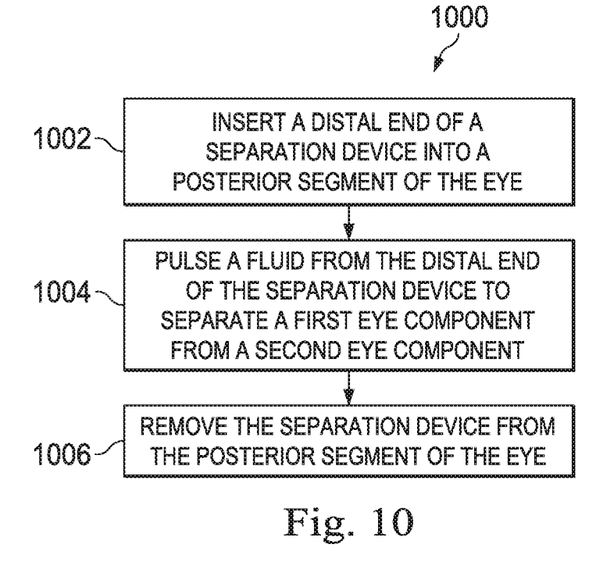
FIG. 10 is a flowchart showing another illustrative method for performing a surgery to separate tissues according to one example incorporating the principles described herein.

Referring now to FIG. 10, shown therein is a flowchart of a method 1000 according to some aspects of the present disclosure. While the method 1000 is illustrated as having elements or operations, embodiments of the method 1000 may include additional elements before, after, in between, and/or as sub-elements of the enumerated elements.

As illustrated in FIG. 10, the method 1000 may begin at 1002 in which distal end of a surgical separation device is inserted into a posterior segment of the eye. As part of the insertion into the eye, a small fenestration or cut may be made in the vitreous cortex to permit a portion of the surgical separation device to be inserted between the posterior vitreous cortex and the ILM.

After the surgical separation device is positioned between the vitreous and the retina of the eye, at 1004, a fluid is pulsed in a series of pulses from the distal end of separation device to separate the first tissue from the second tissue. The series of pulses may each apply pressure between the first and second tissues to separate them without applying substantial shear stress that may damage either of the two tissues. The series of pulses may be provided in response to a request from a user to initiate the series. For example, the user may be a clinician using a surgical system (such as the surgical system 200 of FIG. 2). The clinician may use the foot pedal 210 or may use another interface provided on a hand piece, like the hand piece 214. At 1006, the separation device is removed from the segment of the eye.

Principles described herein can provide several benefits to surgical operations involving the separation of one tissue layer bound together with another tissue layer. For example, use of the series of pulses rather than a mechanical cutting tool limits potential cutting damage to either tissue. The series of pulses can also separate tissue efficiently without subjecting the retina to significant shear stresses, which can cause tearing of the retina. The separation device described herein may also provide for more effective use of active component that dissolve the fibers connecting the layers of tissues.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. Similarly, while examples provided herein may be directed to separating the vitreous from the retina in an eye, the principles of the present disclosure may be applicable to separate other adhered bodily tissues in a safe, effective manner. It is understood that such variations may be made to the foregoing without departing from the scope of the present disclosure. Accordingly, it is appropriate that the appended claims be construed broadly and in a manner consistent with the present disclosure.

What is claimed is:

1. A method of performing a posterior vitreous detachment, the method comprising:
   receiving a command from a user of a surgical system to initiate a detachment process;
   wherein the surgical system comprises a surgical console and a handpiece fluidly coupled to the surgical console;
   wherein the surgical console comprises a fluid reservoir; and
   wherein the handpiece comprises a handle portion configured to be grasped by a user and a flexible elongate lumen coupled to a distal end of the handle portion;
   forcing a first pulse of fluid from the fluid reservoir through the flexible elongate lumen to a surgical site to separate a vitreous from a retina; and
   forcing a second pulse of the fluid from the fluid reservoir through the flexible elongate lumen to the surgical site to further separate the vitreous from the retina, without repositioning the handpiece between the first and second pulses.

2. The method of claim 1, wherein the first pulse of the fluid contains one of:
   air;
   salt solution;
   perfluoro-n-octane; or
   a viscoelastic polymer.

3. The method of claim 1, wherein the first pulse of the fluid has a volume of about 100 microliters or less.

4. The method of claim 1, further comprising:
   receiving a first selection from the user that indicates a pulse volume; and
   receiving a second selection from the user that indicates a pulse pressure, and
   wherein the first pulse of the fluid has the pulse volume and wherein forcing the first pulse of the fluid comprises forcing the first pulse of the fluid at the pulse pressure.

5. The method of claim 4, wherein the first selection from the user is received through a button, toggle switch, or slider on the handpiece.

6. The method of claim 4, wherein the first selection from the user is received through a foot pedal system.

7. The method of claim 1, wherein the first pulse and the second pulse are forced through the flexible elongate lumen having a proximal end and a nozzle at a distal end.

8. The method of claim 1, further comprising directing a series of pulses toward the vitreous through a first side port of a distal end of the flexible elongate lumen and directing the series of pulses toward the retina through a second side port of the distal end of the flexible elongate lumen.

9. The method of claim 1, further comprising inserting a distal end of a separation device into a posterior segment of an eye prior to receiving the command from the user of the surgical system to initiate the detachment process.

10. The method of claim 1, wherein forcing the second pulse of the fluid from the reservoir of the surgical system through the flexible elongate lumen to the surgical site to further separate the vitreous tissue from the retina comprises injecting a series of pulses between a posterior vitreous cortex and an inner limiting membrane (ILM).

11. The method of claim 10, further comprising making a small cut in the vitreous cortex to insert the handpiece between the posterior vitreous cortex and the ILM prior to injecting the series of pulses between the posterior vitreous cortex and the ILM.

\* \* \* \* \*